United States Patent
Voncken et al.

(10) Patent No.: US 10,888,678 B2
(45) Date of Patent: Jan. 12, 2021

(54) CPAP PRESSURIZED GAS PERMEABLE MASK CUSHION

(71) Applicant: KONINKLIJKE PHILIPS N.V., Eindhoven (NL)

(72) Inventors: Rudolf Maria Jozef Voncken, Eindhoven (NL); Jonathan Sayer Grashow, Cheswick, PA (US); Sima Asvadi, Eindhoven (NL); Lauren Patricia Chodkowski, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 354 days.

(21) Appl. No.: 15/507,418

(22) PCT Filed: Aug. 25, 2015

(86) PCT No.: PCT/EP2015/069458
§ 371 (c)(1),
(2) Date: Feb. 28, 2017

(87) PCT Pub. No.: WO2016/030381
PCT Pub. Date: Mar. 3, 2016

(65) Prior Publication Data
US 2017/0281889 A1    Oct. 5, 2017

Related U.S. Application Data

(60) Provisional application No. 62/042,868, filed on Aug. 28, 2014.

(30) Foreign Application Priority Data

Oct. 1, 2014 (EP) .................................. 14187246

(51) Int. Cl.
*A61M 16/06* (2006.01)
*A61M 16/04* (2006.01)

(52) U.S. Cl.
CPC .... *A61M 16/0443* (2014.02); *A61M 16/0452* (2014.02); *A61M 16/06* (2013.01);
(Continued)

(58) Field of Classification Search
CPC .......... A61M 16/0443; A61M 16/0605; A61M 16/0452; A61M 16/06; A61M 16/0622;
(Continued)

(56) References Cited

U.S. PATENT DOCUMENTS 6,467,482 B1 * 10/2002 Boussignac ........... A61M 16/06
128/206.24
8,276,588 B1 * 10/2012 Connor ................. A61M 16/06
128/205.25

(Continued)

FOREIGN PATENT DOCUMENTS

FR    2859383 A1    3/2005
FR    2988003 A1    9/2013
(Continued)

*Primary Examiner* — Timothy A Stanis
*Assistant Examiner* — Thao Tran
(74) *Attorney, Agent, or Firm* — Michael W. Haas

(57) ABSTRACT

A patient-contacting element for a patient interface for delivering a flow of gas to a user is being configured to provide a substantially air-tight seal with the user's skin during use. The patient-contacting element includes an inlet for receiving at least part of the flow of gas, at least one gas-permeable element that is disposed within the patient-contacting element and arranged in fluidic communication with the inlet, and a first layer of an air-tight material that is arranged between the at least one gas-permeable element and an inner space of the patient-contacting element for (Continued)

receiving a nose and/or a mouth of the user. The air-tight material has at least one opening therein.

13 Claims, 6 Drawing Sheets

(52) U.S. Cl.
CPC .... *A61M 16/0605* (2014.02); *A61M 16/0616* (2014.02); *A61M 16/0622* (2014.02); *A61M 16/0633* (2014.02); *A61M 16/0683* (2013.01)

(58) Field of Classification Search
CPC .......... A61M 16/0683; A61M 16/0633; A61M 16/0616; A61M 16/0661; A61M 16/0611
See application file for complete search history.

(56) References Cited

U.S. PATENT DOCUMENTS

| | | | | |
|---|---|---|---|---|
| 2003/0172932 | A1* | 9/2003 | Matioc | A61M 16/06 128/206.24 |
| 2004/0211428 | A1* | 10/2004 | Jones, Jr. | A61M 16/0605 128/206.27 |
| 2004/0216747 | A1* | 11/2004 | Jones, Jr. | A61M 16/065 128/206.21 |
| 2006/0237018 | A1 | 10/2006 | McAuley | |
| 2011/0247625 | A1* | 10/2011 | Boussignac | A61M 16/0622 128/205.25 |
| 2011/0297152 | A1 | 12/2011 | Duveen | |
| 2012/0132208 | A1* | 5/2012 | Judson | A61M 16/06 128/205.25 |
| 2013/0008445 | A1* | 1/2013 | Boussignac | A61M 16/0622 128/205.25 |
| 2013/0139822 | A1* | 6/2013 | Gibson | A61M 16/0616 128/205.25 |
| 2013/0192601 | A1 | 8/2013 | Reischl | |
| 2015/0040909 | A1* | 2/2015 | Willard | A61M 16/0633 128/205.25 |
| 2015/0265795 | A1* | 9/2015 | Voncken | A61M 16/0655 128/206.24 |
| 2016/0008566 | A1* | 1/2016 | Partington | A61M 16/0875 128/201.13 |
| 2016/0095996 | A1* | 4/2016 | Gusky | A61M 16/125 128/205.25 |

FOREIGN PATENT DOCUMENTS

| | | |
|---|---|---|
| WO | WO9925410 A1 | 5/1999 |
| WO | WO2004041342 A1 | 5/2004 |
| WO | WO2005028010 A2 | 3/2005 |
| WO | WO2007068044 A1 | 6/2007 |
| WO | WO2010028425 A1 | 3/2010 |
| WO | WO2011003128 A1 | 1/2011 |
| WO | WO2013108145 A1 | 7/2013 |
| WO | WO2013144753 A1 | 10/2013 |
| WO | WO2013171624 A1 | 11/2013 |
| WO | WO2014020468 A1 | 2/2014 |

* cited by examiner

CPAP PRESSURIZED GAS PERMEABLE MASK CUSHION

CROSS-REFERENCE TO RELATED APPLICATIONS

This patent application claims the priority benefit under 35 U.S.C. § 371 of international patent application no. PCT/EP2015/069458, filed Aug. 25, 2015, which claims the priority benefit under 35 U.S.C. § 119(e) of U.S. Provisional Application No. 62/042,868 filed on Aug. 28, 2014 and European Patent Application No. EP 14187246.5, filed Oct. 1, 2014, the contents of which are herein incorporated by reference.

FIELD OF THE INVENTION

The present invention pertains to a patient-contacting element for a patient interface for delivering a flow of gas to a user, the patient-contacting element being configured to provide a substantially air-tight seal with the user's skin during use. Further, the present invention relates to a patient interface including such a patient-contacting element.

BACKGROUND OF THE INVENTION

Patient interfaces, such as masks in pressure support systems, are used for delivering gas to a user. Such gases like air, cleaned air, oxygen, or any modification thereof are submitted to the user (also referred to as patient) via the patient interface in a pressurized or unpressurized way.

For several chronic disorders and diseases the usage of such a patient interface is necessary or at least advisable.

One example of such a disease is obstructive sleep apnea or obstructive sleep apnea syndrome (OSA). OSA is usually caused by an obstruction of the upper airway. It is characterized by repetitive pauses in breathing during sleep and is usually associated with a reduction in blood oxygen saturation. These pauses in breathing, called apneas, typically last 20 to 40 seconds. The obstruction of the upper airway is usually caused by reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied with snoring.

Different invasive and non-invasive treatments for OSA are known. One of the most powerful non-invasive treatments is the usage of Continuous Positive Airway Pressure (CPAP) or Bi-Positive Airway Pressure (BiPAP) in which a patient interface, e.g. a face mask, is attached to a tube and a machine that blows pressurized gas, preferably air, into the patient interface and through the airway of the patient in order to keep it open. Positive air pressure is thus provided to a patient through a hose connected to a patient interface or respiratory interface, such as a face mask, that is worn by the patient regularly at night. The afore-mentioned long-term use of the patient interface is the result, since the wearing of the patient interface usually takes place during the sleeping time of the patient.

Examples for patient interfaces are:
nasal masks, which fit over the nose and deliver gas through the nasal passages,
oral masks, which fit over the mouth and deliver gas through the mouth,
full face masks, which fit over both, the nose and the mouth, and deliver gas to both, and
nasal pillows, which are regarded as masks as well within the scope of the present invention and which consist of small nasal inserts that deliver the gas directly to the nasal passages.

In order to guarantee a reliable operation of the device, the patient interface needs to closely fit on the patient's face to provide an air-tight seal at the mask-to-face interface. Usually, the patient interface is worn using a headgear with straps that go around the back of the patient's head. The patient interface or mask in practice usually comprises a soft cushion that is used as mask-to-patient interface, i.e. that contacts the face of the patient when the mask is worn, as well as it usually comprises a so-called mask shell building a rigid or semi-rigid holding structure for holding the cushion in place and for supplying mechanical stability to the patient interface.

The cushion usually comprises one or more pads made of gel or silicon or any other soft material in order to increase the patient comfort and guarantee a soft feeling on the patient's face. The later mentioned mask shall usually also comprise a hose interface that is adapted for connecting their supplying hose to the mask. Depending on the type of the mask, it may also comprise a mechanism with an additional cushion support on the forehead to balance the forces put by the mask around the airway features of the human face. For current CPAP masks the cushion typically comprises a thin-walled silicon structure that is compressed into the face in order to create an air-tight seal with the face. Additionally, some masks also include a secondary structure constructed from silicon or another material, such as a gel-filled bladder, to provide underlying support for the silicon sealing structure. The function of these support structures is to further increase the contact pressure between the cushion and the face by transmitting compressive forces to the face through the silicon sealing structure.

Since the above-mentioned patient interfaces are usually worn over night and on a long-term basis, it is evident that users of CPAP masks experience one or more disadvantages bearing such masks over night where the most prominent are mask discomfort and facial red marks. These disadvantages arise due to preventing leakage and ensuring sufficient mask stability by providing sufficient contact pressure between mask sealing structure and face.

In the art difficulties relating to uncomfortable pressure points and skin markings, such as red marks, indentations, and overall prolonged discomfort have been addressed by providing a cushion which is not subject to the lateral movement upon changing from a relaxed to a compressed position.

WO 2014/020468 A1 informs about such a mask including a cushion for a patient interface device. Between a patient-contacting element and a coupling portion to the frame of a patient interface a wall portion is provided having a base portion extending from the coupling portion and an angled portion extending from the base portion outwardly, an underlying support portion extending from a mid-portion of the angled portion, and a membrane extending from an end of the angled portion opposite the base portion. The angled portion is structured to maintain lateral positioning of the membrane and a support portion when the cushion is transitioned from an uncompressed position to a compressed position.

WO 2011/003128 A1 discloses a cushion for a respiratory mask. The mask cushion is used for delivering breathable gas to a patient's airways and comprises a chamber and an inner cushion component. An outer barrier or membrane serving as patient contact side is applied to the inner cushion component to form the chamber. The chamber comprises a fluid or gas. The inner cushion component may be an open cell or closed cell foam. The mask cushion may have a chamber supply duct guiding air through the inner cushion component to the chamber to pressurize the same.

WO 2007/068044 A1 discloses a cushion for a patient interface comprising at least two bladders arranged in concentric relation and adapted for independent pressurizing.

Given the spread in facial geometry, variants in mask strapping forces and disturbing factors such as external forces acting on the mask due to pillow contact, it is very difficult to ensure that a cushion compression at all positions is an optimal compression range.

To prevent leakage and ensure enough mask stability, a minimum contact pressure is needed between mask sealing structure and face. This minimum contact pressure will be equal to the used CPAP pressure. On the other hand, a contact pressure that is too high will lead to red marks and eventually even to pressure ulcers.

SUMMARY OF THE INVENTION

It is therefore an object of the invention to provide patient interfaces or components thereof which reliably seal the structure against the face of the user without causing pressure points, red marks, and/or any other discomfort. Another objective resides in the provision of a patient interface or component thereof giving the mask a stable position with respect to the user's face. Still another objective is the provision of a patient interface or component thereof accurately and evenly maintaining sealing contact at essentially all contacting points with the user's face.

In a first aspect of the present invention a patient-contacting element for a patient interface for delivering a flow of gas to a user is provided. Said patient-contacting element is configured to provide a substantially air-tight seal with the user's skin during use and comprises:
an inlet for receiving at least part of the flow of gas, and
at least one gas-permeable element that is disposed within the patient-contacting element and arranged in fluidic communication with the inlet. The patient-contacting element further comprises a first layer of an air-tight material that is arranged between the at least one gas-permeable element and an inner space of the patient-contacting element for receiving a nose and/or a mouth of the user, wherein the air-tight material has at least one opening therein.

In a further aspect of the present invention a patient interface for delivering a flow of gas to the user is presented, said patient interface comprises the present patient-contacting element.

The invention therefore overcomes the above-mentioned disadvantages by providing the present patient-contacting element comprising a soft, air-permeable material disposed within the patient-contacting element and which allows for flowing in the internal CPAP air flow with the CPAP pressure. In this way minimum required contact pressure with the face is ensured (equal to the CPAP) and stress concentrations are avoided due to the softness of the material. The use of at least one gas-permeable element permits non-constant cushion or patient-contacting element compression stiffness which significantly increases the optimal compression range and assists in realizing compression at all places of the user's face in an optimal compression range.

The primary advantage of the present arrangement is that exactly the required minimum pressure for sealing will be realized for all different values of the CPAP pressure. In this way the sealing structure automatically adjusts contact pressure with the face when the CPAP pressure changes. This means the contact pressure of the mask will increase and the seal will be maintained when the CPAP pressure increases, such as with an auto-titrating CPAP and/or ramp feature.

The at least one gas permeable element may be arranged within the interior of the patient-contacting element and accounts for the substantially air-tight seal with the user's skin that is provided by the patient-contacting element.

The minimum contact pressure exerted by the patient interface or mask onto the face is equivalent to the minimum required sealing pressure. This means that minimum compression of the cushion is required to achieve a seal. Accordingly, depth of the cushion (in a compression direction) can be minimized since only minimal "pre-loading" is required to achieve the required contact pressure for a seal. Hence, straps or other fastening means employed for reliably attaching the present patient-contacting element or patient interface to the user's face require minimal contact pressure. Additionally, the stiffness of the gas-permeable element can be optimized for accommodating facial variability and mask stability, i.e. the cushion may undergo a wide range or compression without exceeding the red mark contact pressure threshold, to a much greater degree than a traditional structure. In addition, the outer layer of the cushion may be chosen from a very soft material and put under a pre-stress, by e.g. compressing the cushion inside material, for avoiding wrinkles.

A patient-contacting element for a patient interface may be understood as any component which is either in the direct contact with the skin of the user upon wearing the same or in close vicinity thereto. The patient-contacting element may be for instance the cushion or any other skin-contacting material formed or made thereon. The patient-contacting element may also correspond to the mask shell and/or to its support.

The patient-contacting element is configured to provide a substantially air-tight seal with the user's skin. The substantially air-tight seal with the user's skin permits inflating of the gas-permeable element in response to the flow of gas provided via the inlet. It may be, however, possible and desired that a certain amount of gas provided passes through the gas-permeable element and contacts the skin of the user.

The term "substantially" as used in the present application generally denotes an air-tight seal with respect to any other structure, such as the user's skin. Substantially air-tight indicates that at least 90% or more, preferably 95% or more, 98% or more or 99% or more of air are retained within the gas-permeable element. In other words, less than 10% of air may pass the substantially air tight seal. Alternatively, the term "substantially" may be understood being directed to a sufficient air pressure maintained within the patient-contacting element and an adequate air flow provided to the user. Hence, substantially air-tight may denote that an air flow of 0.1 L/min or more is provided to the user. Preferably an air flow of 1 L/min or more, 10 L/min or more, or even 50 L/min or more is provided to the user. Complete air-tight seal with the user's skin is also conceivable. The substantially air-tight seal with the user's skin enables maintaining of the at least one gas-permeable element in an inflated state and provides at the same time a cooling flow of air at a contacting part of the patient-contacting element and assists in keeping the skin dry which in turn facilitates avoiding skin irritations, such as red marks and ulcers.

The patient interface may either design for the mask or individual parts thereof. The patient interface may for example have two members interconnected with each other, one of the members comprising a cushion for contacting a face of the user and wherein the other member comprises a mask shell for holding the cushion. The cushion may have a skin-contacting material or may be prepared thereof. The skin-contacting material may be also denominated sealing flap hereinafter.

An inlet for receiving at least part of the flow of gas as used therein may be any kind of port for providing the at least one gas-permeable element with gas. Gas as used herein refers to conventional breathing air or synthetic air. Synthetic air may encompass breathing air wherein one or more constituents, such as oxygen, are enriched or depleted. Synthetic air may also comprise any breathable mixture, such as a mixture consisting of oxygen and nitrogen only under the proviso that sufficient oxygen is contained.

The at least one gas-permeable element is arranged in fluidic communication with the inlet. The at least one gas-permeable element may be made of a foam and/or a stack of spacer fabrics. As foam may serve for example an open cell foam. The gas-permeable element is preferably shaped to improve the fit of the patient-contacting element on a user's face or head for providing optimal contact with the user's face. In general, the material of the patient-contacting element is not particularly restricted, as long as it is inflatable and deflatable in dependence from the flow of gas provided via the inlet and the material of the gas-permeable element changes its volume in response to the pressure of the flow of gas provided. Hence, the patient-contacting element may have a sponge-like, comb-like structure or any other kind of porous structure wherein the pores are at least partially interconnected to permitting flow of gas.

The patient-contacting element may further have a layer covering at least a portion of the at least one gas-permeable element to ensure air-tightness. Alternatively or in addition, the material of the sponge, comb and/or pores exhibits sealing properties in an outer portion thereof ensuring that essentially the complete gas-permeable element may be inflated, i.e. expanded, or deflated, e.g. shrinked.

The expression "at least one" is used to designate essentially any number encompassing for example 2, 3, 4, 5, 6, 7, 9, or 10 individual items, such as gas-permeable elements. However, the use of a single gas-permeable element encompassing all the contacting area with the user's face is preferred.

The expression "air-tightness" as used herein may refer to air as such. However, any kind of synthetic air may be encompassed as well.

According to one embodiment of the present invention, the patient-contacting element comprises at least one further layer of an air-tight material covering at least a portion of the at least one gas-permeable element.

The at least one further layer of an air-tight material covering at least a portion of the at least one gas-permeable element prevents leaking of gas through the patient-contacting element at undesired areas. Such areas may encompass the contact-surface with the user's skin and/or an area of the patient-contacting element which is in connection with the outer space or environment. Alternatively or in addition, a layer of an air-tight material may share the gas-permeable element from the inner space of the patient-contacting element which inner space receives a nose and/or mouth of the user. The layer's material may be a highly elastic material, such as polymer films, polymer membranes, closed cell foams, and air-tight or coated textile fabrics, which may be easily compressed. Alternatively, the layer is chosen sufficiently thin and made of a material such as polyurethane or silicone with the consequence that compression and wrinkling takes place at the side walls of the cushion which are not in contact with the user's face. Another possibility is in pre-stressing the layer, thereby compressing the inside of the cushion, which assists in avoiding wrinkles. The skilled person is well aware about the materials used for such a layer of an air-tight material and the required thickness.

The first layer of an air-tight material may comprise essentially each kind of air-tight materials of flexible nature. Examples for such air-tight materials comprise inter alia polymer films, polymer membranes, closed cell foams and coated textile fabrics. The first layer of an air-tight material provides a boundary layer between the at least one gas-permeable element and an inner space of the patient-contacting element. Hence, the first layer of an air-tight material may form part of the patient-contacting element and shares the patient contacting element from the mouth and/or nostrils of the user. The at least one opening formed in the first layer of the air-tight material has a diameter permitting sufficient flow of gas received via the inlet to the at least one gas-permeable element to permit its inflation and deflation in response to the changing of flow of gas and/or to the contacting pressure of the patient-contacting element to the user's face.

The at least one opening comprises essentially any number of openings. For example a number of 1 to 10000, preferably 1 to 1000, 50 to 500, or 100 to 200 openings may be provided in the boundary layer between the at least one gas-permeable element and the inner space of the patient-contacting element. Alternatively, a porous material may be used for forming the first layer of an air-tight material wherein number, diameter and distribution of the pores may be chosen according to the actual requirements.

As already indicated above the first layer of an air-tight material may provide flow of gas essentially in both directions. Depending on the structure of the patient-contacting element it may be, however, that only one direction of flow is achieved. The inlet for receiving at least part of the flow of gas may be for example provided directly to the gas-permeable element and via the gas-permeable element through the at least one opening formed in the first layer of an air-tight material to the user. Hence, this example describes the case wherein the flow of gas provided to the user exclusively flows through the gas-permeable element.

Alternatively, the patient-contacting element may be adapted to split the flow of gas in different parts, wherein a required part is provided directly to the user and at least another part of the flow of gas is provided to the at least one gas-permeable element. Hence, part of the flow of gas is exclusively used for inflating the at least one gas-permeable element. The flow of gas provided to the gas-permeable element may be further partially pass the substantially air-tight seal with the user's skin. As indicated above this may provide an advantageous cooling and drying effect to the user's skin for increasing the mask's comfort and reducing the danger of forming red marks.

Pressure built up in the at least one gas-permeable element may be also reduced by providing a flow of gas to the outer space of the patient-contacting element. Also a combination of the two possibilities indicated above, i.e. providing a part of the flow of gas to the user's skin and another part to the outer space of the patient-contacting element, is conceivable.

According to another embodiment of the present invention, the patient-contacting element comprises a second layer of an air-tight material that is arranged between the at least one gas-permeable element and an outer space of the patient-contacting element which is not in fluidic communication with the flow of gas during use.

The second layer may thus form part of the boundary-layer between the inner space of the patient-contacting element and the environment/outer space. Hence, the second layer prevents leaking of gas to the environment upon use. The second layer may be formed for example of a material selected from a group consisting of a polymer film, a polymer membrane, a closed cell foam and a coated textile fabric.

It may be clear that the above-mentioned first layer and second layer are not necessarily required, as the leaking properties of the at least one gas-permeable element may be influenced by its material and in particular by the material used for forming the boundary to the user's skin and/or the outer space. As already indicated above the at least one gas-permeable element may be formed for example from a foam and/or stack of spacer fabrics. The pore size and/or distance of stacks of spacer fabrics may be for example reduced at an area of the at least gas-permeable element towards the user's skin the inner space and/or outer space. Hence, a single material may be chosen wherein the gas-permeability in the boundary layers towards the user's skin, the inner space and outer space may be individually adapted according to the current needs. This permits forming the patient-contacting element in a manner that an equal and minimal pressure on all parts of the user's face is obtained. In addition, forming of another first and/or second layer on the at least one gas-permeable element may be omitted and facilitating producing of gas-permeable elements.

According to one embodiment of the present invention, the inlet opens out directly into the at least one gas-permeable element in order to provide at least part of the flow of gas directly to the at least one gas-permeable element. Hence, a part of the flow of gas is provided exclusively via the at least one gas-permeable element to the user. This provides the advantage of using the at least one gas-permeable element for pressure reduction. Hence, the at least one gas-permeable element may be adapted for providing the required end pressure to the user.

Alternatively, the at least one gas-permeable element may comprise moisture uptake means and/or anti-microbial agents. Moisture uptake means advantageously uptake humidity from the user's air, thereby reducing moisture between the contacting area between the patient-contacting element and the user's skin. This assists in increasing comfort and reducing the danger of forming red marks. Anti-microbial agents inhibit growth of microorganisms which may otherwise infect portions of the skin and give raise to skin irritations. Moisture uptake means and anti-microbial agents are usually subject to loss and/or decomposition with the consequence that the at least one gas-permeable element needs to be exchanged after a certain time of use. Accordingly, it is preferred to provide the at least one gas-permeable element in releasable connection with the patient-contacting element to enable exchange thereof.

Hydrophilic polymer material, such as a hydrophilic silicon rubber material may be used as moisture uptake means. The anti-microbial agents include for example one or more of anti-bacterial, anti-fungal agents and anti-viral agents. Examples of anti-bacterial agents comprise silver compounds and alpha-olefin sulfonates. Preferably, a material is used combining both of the above-mentioned functionalities, i.e. a moisture uptake means and an anti-microbial agent, such as a hydrophilic material which is an alpha-olefin sulfonate containing-filled silicon rubber.

According to still another embodiment of the present invention the patient-contacting element is selected from the group consisting of a cushion, a forehead pad, a headgear and a cheek-mounted support. Such patient-contacting elements are well known to a skilled person.

According to one embodiment of the present invention, the at least one gas-permeable element comprises a foam and/or a stack of spacer fabrics. The foam is preferably an open cell foam providing flow of gas within the at least one gas-permeable element. As noted above the foam and/or stack of spacer fabrics may be adapted to the current needs, i.e. by adapting the diameter of pores within the foam as well as the interconnection of the pores. The same holds true with respect to the stack of spacer fabrics, wherein the distance between the stacks and the fabric properties influence the flow of gas within the at least one gas-permeable element.

Alternatively, the properties of the foam and/or stack of spacer fabrics may be varied above the patient-contacting element. Hence, the patient-contacting element may have different gas-permeable properties at different parts of the patient-contacting element with respect to the position on the user's skin/face. In addition, the properties of the foam and/or stack of spacer fabrics may be varied within a particular gas-permeable element to provide different degrees of air-tightness with respect to at least one of the user's skin, inner space and outer space of the patient-contacting element. Hence, the patient-contacting element may comprise essentially a single gas-permeable element which has different degrees of air-tightness with respect to the inner part of the mask, the environment and the user's skin. A single material may be used for this purpose.

According to another preferred embodiment, the foam is an open cell foam.

According to still another embodiment of the present invention, a shape of the at least one gas-permeable element is adapted to contour of a user's face or head. This is well within the knowledge of the skilled person and assists in increasing the user's comfort and guarantees a soft feeling on the face.

According to one embodiment of the present invention, properties of the at least one gas-permeable elements vary along the at least one gas-permeable element. This permits adapting the properties with respect to skin properties and/or pressure requirements at different parts of the user's skin. Hence, a patient interface may be provided, wherein the patient-contacting element requires a minimum of contacting pressure, achieving however the required functionality of the patient interface. Such a patient-contacting element and/or patient interface provides thus a high comfort to the user. In addition, the danger of forming red marks and ulcers is significantly reduced.

According to one embodiment of the present invention, the patient-contacting element comprises a plurality of gas-permeable elements. The patient-contacting element may comprise for example 2, 3, 4, 5, 6, 7, 8, 9, 10 or more individual gas-permeable elements.

According to another embodiment of the present invention, the patient-contacting element comprises a third layer which covers at least a portion of the patient-contacting element and provides the substantially air-tight seal with the user's skin during use. Substantially air-tight seal with the user's skin is obtained by providing a third layer of a material selected from the group consisting of a polymer film, a polymer membrane, a closed cell foam and accorded textile fabric.

These materials provide substantial air-tight seal with the user's skin, e.g. to at least 90% or more, permit generation of sufficient pressure within the patient-contacting element and in particular the gas-permeable element.

The third layer covering at least a portion of the patient-contacting element and providing the substantially air-tight seal with the user's skin during use may be also provided by modifying an outer layer of the at least on gas-permeable element, wherein the outer layer is in close vicinity of the skin. Such a modification may encompass for instance (thermally) sealing the pores of an open cell foam used as material for the at least on gas-permeable element. It will be appreciated that such sealing of the pores has essentially the same effect as providing a layer of another material between the gas-permeable element and the user's skin. Such sealing of the pores enables omitting the necessity of provide an additional layer of material.

According to still another embodiment of the present invention, the third layer comprises a polymer film, a polymer membrane, a closed cell foam and/or a coated textile fabric. Preferably, the polymer film is a polyurethane film or silicone film. These materials are well known to the skilled person and have the advantage that the use for preparing patient-contacting elements or parts thereof is well known in the art.

According to an embodiment of the present invention, the third layer is configured to provide openings therein which openings provide a flow of gas to the user's skin upon use. The material of the third layer as well as the number of openings and their orientation is known to the skilled person. Alternatively, the third layer may be omitted and the at least one gas-permeable element may be modified in a region forming the skin contact. This modification encompasses providing substantial air-tightness.

Preferably, the first layer may partially overlap the second layer. Alternatively, the first layer may partially overlap the third layer. Still alternatively, the second layer may partially overlap the third layer. More preferred, the first layer partially overlaps the second layer and third layer, and the second layer partially overlaps the third layer.

According to still another preferred embodiment, a patient interface for delivering a flow of gas to a user is provided. Said patient interface comprises a patient-contacting element according to the present invention.

BRIEF DESCRIPTION OF THE DRAWINGS

These and other aspects of the invention will be apparent from and elucidated with reference to the embodiment(s) described hereinafter. In the following figures examples are purely illustrative of specific embodiments should not be understood as limiting the scope of invention. In the following drawings

DETAILED DESCRIPTION OF THE INVENTION

Figure 1:
FIG. 1 shows an example of a patient interface according to the present invention.

FIG. 1 shows an example of a mask according to the present invention. The main structural elements of the mask shown in FIG. 1 are generally known and not particularly designated. The embodiments according to the present invention are shown in FIGS. 3 to 7. However, FIG. 1 shall give an overview of the main structural elements comprised in a patient interface.

The patient interface is in FIG. 1 in its entirety denoted with reference numeral 12. The mask 12, in the following also referred to as patient interface 12, is typically used in pressure support systems (CPAP systems). That is to supply a flow of gas to the airway of a patient 50. Such patient interfaces are well known and are mostly worn on the head using a strap system around a patient's head to hold the mask 12 in place around the airway entry features of the human face. The patient interface 12 typically comprises a rigid or semi-rigid mask shell to which the headgear/strap system is attached. The mask shell is usually made of a rigid or semi-rigid material, such as e.g. plastic, polycarbonate or silicon. However, also other materials are generally conceivable. The mask shell serves as a holding frame for holding a flexible soft cushion/mask flap 10, also referred to as patient-contacting element.

The patient-contacting element 10 engages the patient's face wherein the mask/patient interface 12 is attached to the patient's face during use. It serves as mask to patient interface.

These patient-contacting elements 10 or cushions 10 are made in the art out of silicon and comprise one or more gel pads in order to establish a soft contact on the patient's face. A further function of these cushions 10 is the sealing of the interior of the patient's interface 12 to the exterior surrounding in order to prevent air leaks between the patient's interface 12 and the patient's face when pressure is applied to the patient's airway. The shape of the cushion/mask flap 10 is thereto preferably adapted to the shape of the user's face. The patient-contacting element 10 may not only be embodied as cushion, but may be also in form of a forehead pad 24, a headgear and a cheek-mounted support.

Figure 2A:
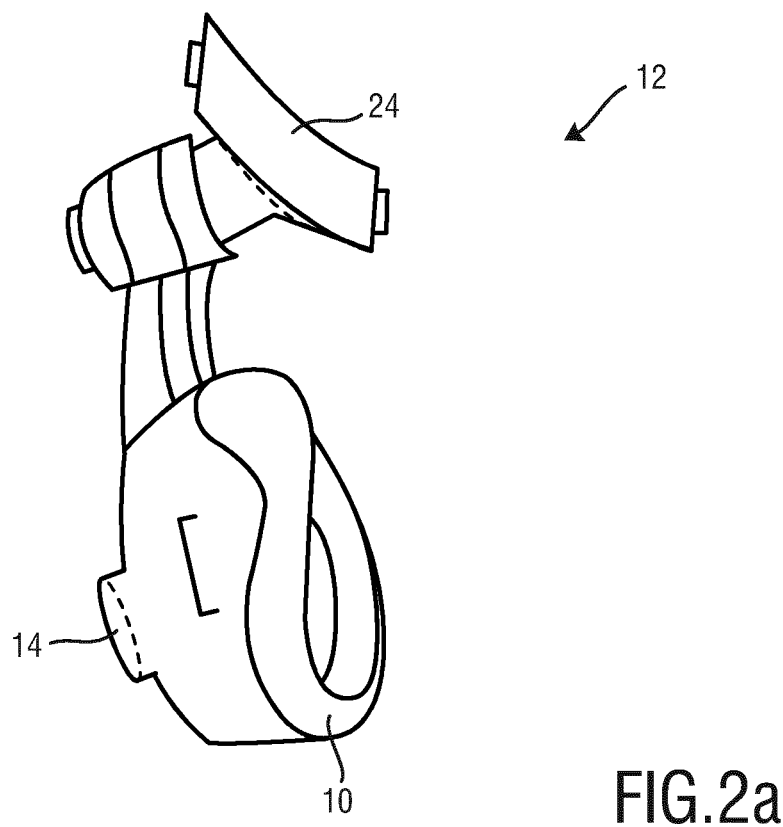
FIGS. 2a and b schematically illustrate a first embodiment of the patient interface according to the present invention.
Figure 2B:
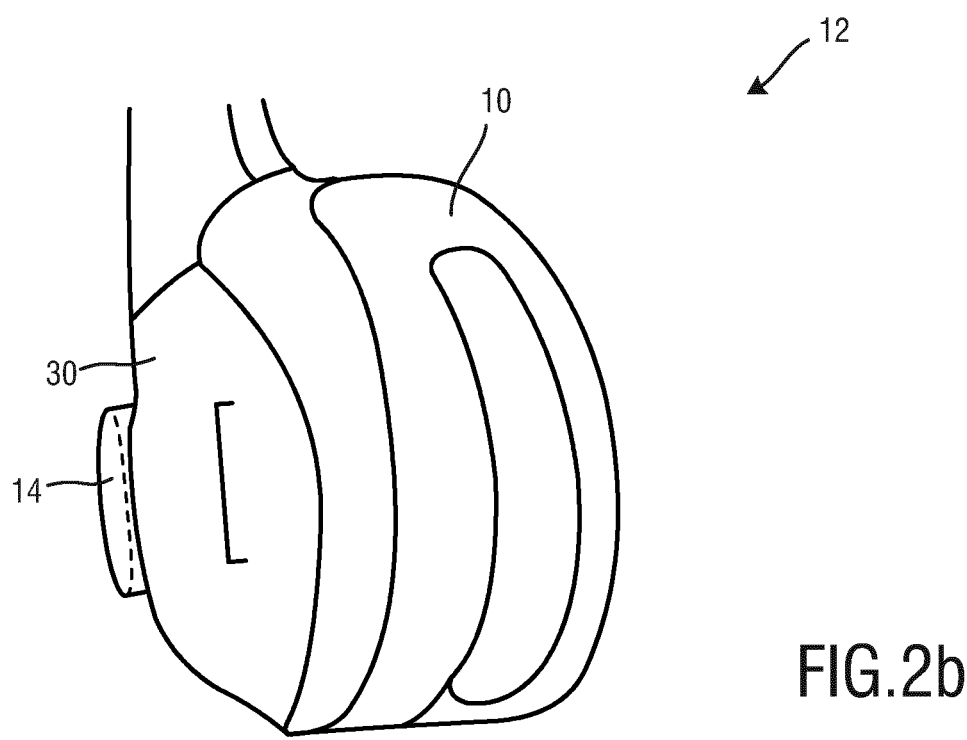

The example illustrated in FIGS. 1, 2a and 2b refers to a so-called full-face mask 12 wherein the cushion/mask flap 10 surrounds the nose and mouth of the user 50. These full-faced masks 12 often comprise an additional cushion support 24, also referred to as forehead support 24, which may be integrally connected to the mask shell, and which is arranged to engage the forehead of the patient 50. The additional cushion support/forehead support 24 mainly serves to balance the forces that the mask 12 exerts on the face of the patient 50 and is mechanically stabilized to mask shell as well as to serve or correct a comfortable fit of the mask. A gas supplying hose (not shown) is usually connected to a connection interface 14 that is preferably attached to or integrated into the mask shell 30. The mask may include the patient-contacting element according to the present invention.

Figure 3:
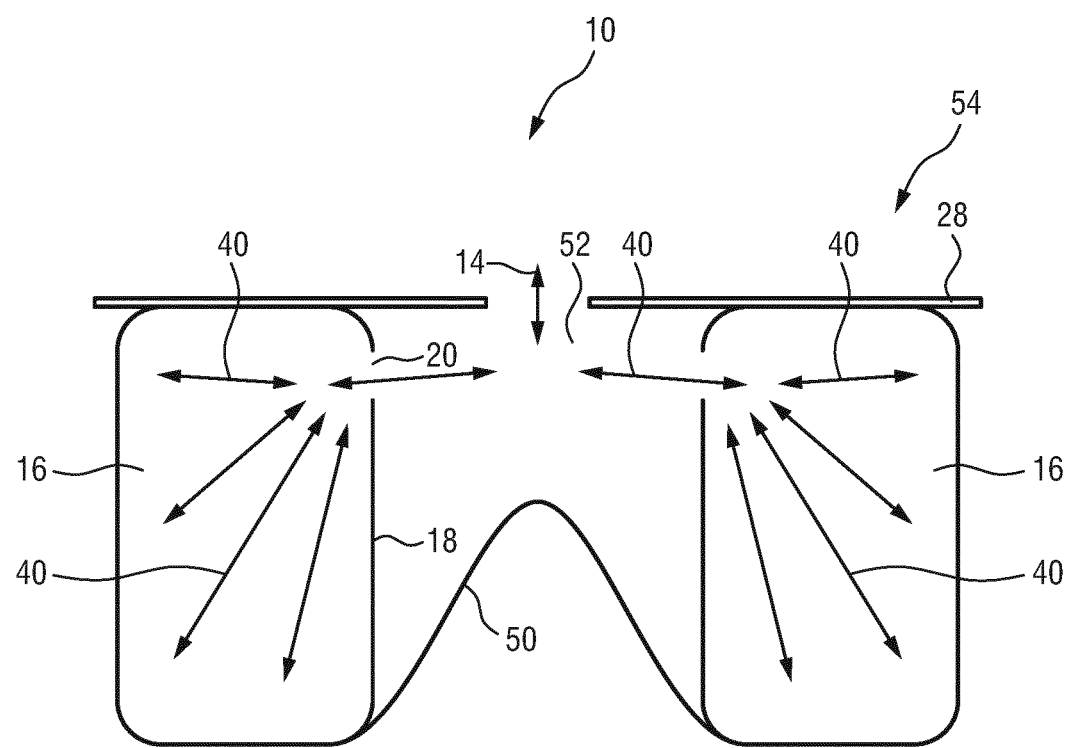
FIG. 3 schematically illustrates the position of a skin contacting element with respect to the user's skin and the flow of gas therein according to a first embodiment.

As illustrated in FIG. 3 a patient-contacting element according to the present invention is shown in cross-section of the air-permeable mask cushion 10 configured to provide a substantially air-tight seal with the user's skin during use. This may be obtained by providing a thin layer of a substantially air-tight material, such as a silicone film, on the contacting area with the skin/face of the user 50. Other materials are also conceivable for the layer such as any kind of polymer film, polymer membrane, closed cell foam or coated textile fabric. The patient-contacting element 10 comprises in this example two gas-permeable elements 16 which are disposed within the patient-contacting element and contact the thin layer of a substantially air-tight material or substantially air-tight boundary. However, any number of gas-permeable elements 16 may be employed. Gas 40 is provided via an inlet 14 and passes from the inner space 52 of the patient-contacting element 100 to the gas-permeable elements 16 through an opening 20 provided in a first layer 18 of a substantially air-tight material sharing the gas-permeable element 16 from the inner space 52 of the patient-contacting element 10. It is clear that the number of openings 20 is not particularly restricted. In general, any number of openings 20 may be employed. Within the gas-permeable elements 16 flow of gas is possible in essentially all directions as indicated by reference number 40. The gas may also stream out the gas-permeable element 16 through opening 20. A silicon sealing flap 28 may be formed between the inner space 52 of the patient-contacting element and the outer space 54.

Figure 4:
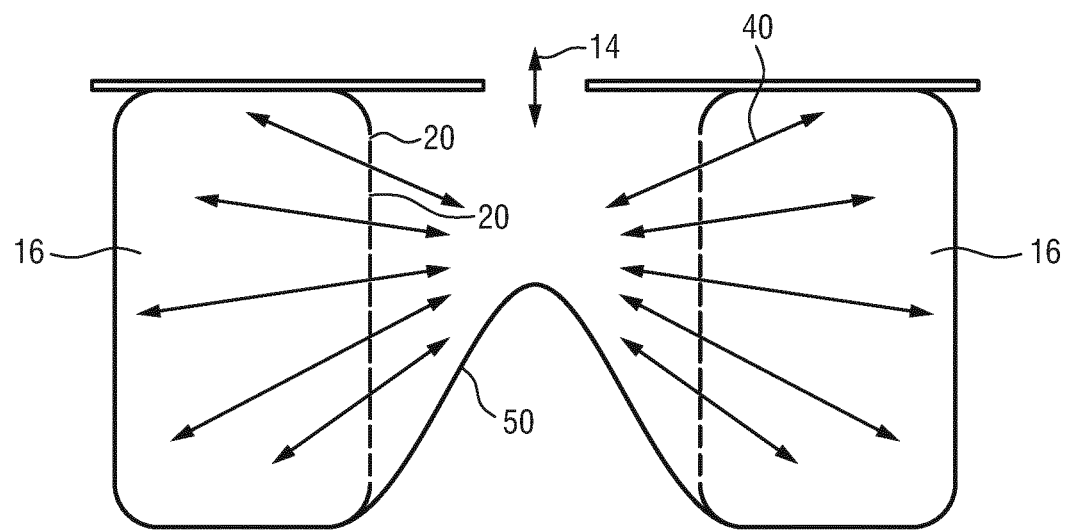
FIG. 4 schematically illustrates the position of a skin contacting element with respect to the user's skin and the flow of gas therein according to a second embodiment.

FIG. 4 shows another embodiment of the present invention. The schematically shown patient-contacting element 10 comprises two gas-permeable elements 16 provided with several openings 20, respectively, which are in fluidic connection with the inner space of the patient-contacting element. The inlet 14 receives at least part of the flow of gas 40 and provides a part of flow of gas 40 to the gas-permeable elements 16 via openings 20. Again, the cushion 10 is configured to provide a substantially air-tight seal with the user's 50 skin during use.

Figure 5:
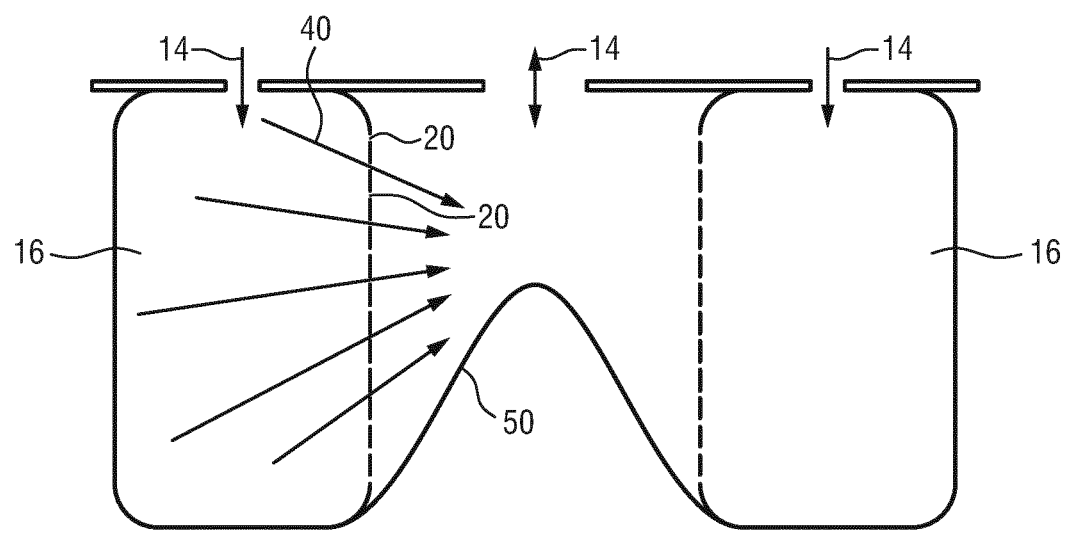
FIG. 5 schematically illustrates the position of a skin contacting element with respect to the user's skin and the flow of gas therein according to a third embodiment.

FIG. 5 still shows another embodiment of a schematically shown patient-contacting element comprising three inlets 14 one of them directly connected with the inner part of the cushion for providing air directly to a user 50. Two other inlets 14 provide air directly to two gas-permeable elements 16, respectively. The part of flow of gas provided to each of the gas-permeable elements 16 leaves the gas-permeable element 16 through openings 20 to the inner space of the contacting element which is indicated by reference number 40 describing an unidirectional flow of gas.

Figure 6:
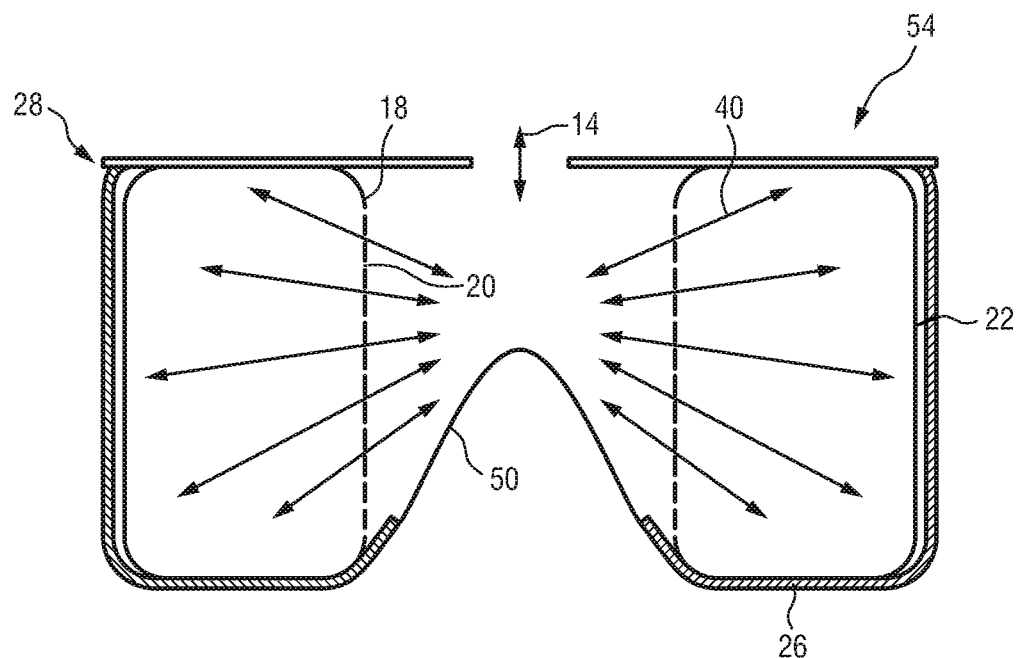
FIG. 6 schematically illustrates the position of a skin contacting element with respect to the user's skin and the flow of gas therein according to a fourth embodiment.

The patient-contacting element 10 exemplarily shown in FIG. 6 may function as a support structure for traditional silicon sealing flaps, such as sealing flap 28 attached to the face of support. The patient-contacting element 10 has two silicon sealing membranes 22, 26 sharing each of the gas-permeable elements 16 from the outer space 54 and user's 50 skin/face. A flow of gas 40 is provided via inlet 14 to the gas-permeable elements 16. The first layer 18 of a substantially air-tight material between the gas-permeable element 16 and the inner space 52 of the patient-contacting element has several openings 20 provided therein permitting bidirectional flow of gas thereby enabling changing of the pressure within the gas-permeable elements 16.

Figure 7A:
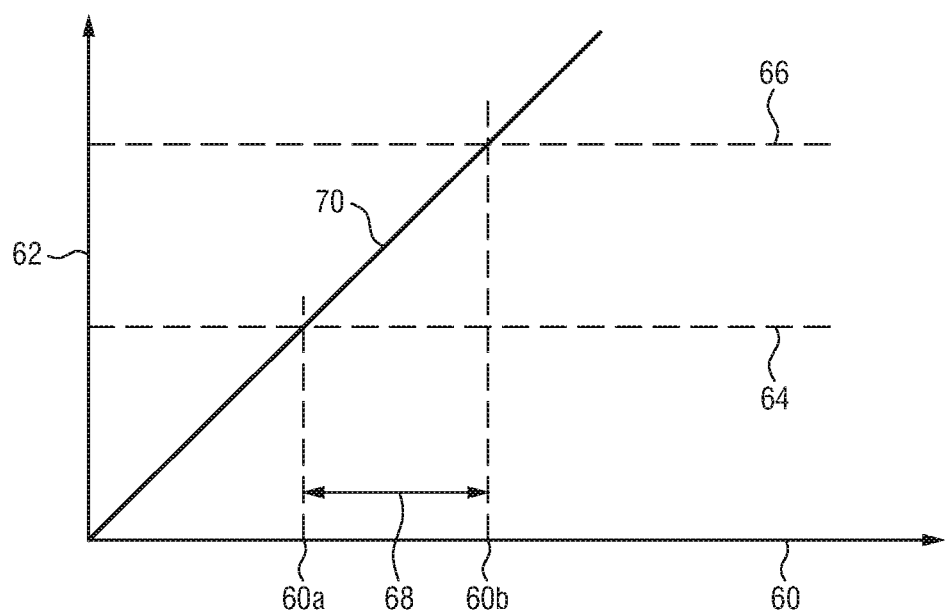
FIGS. 7a to 7c show the optimal compression ranges for constant cushion stiffness, non-constant cushion stiffness and air-assisted cushion stiffness, respectively.
Figure 7B:
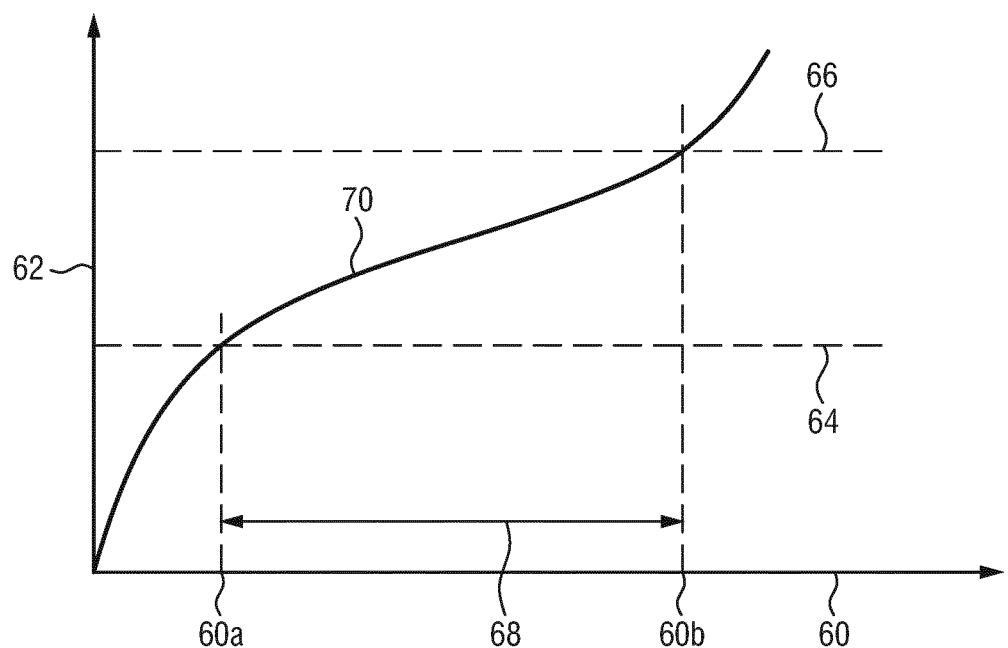
Figure 7C:
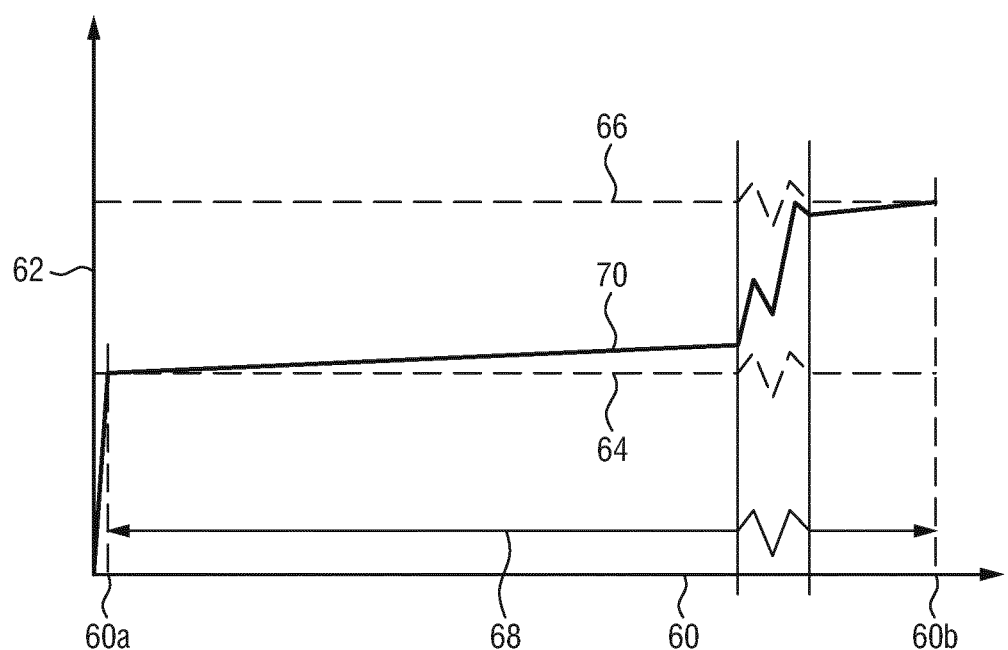

FIGS. 7a to c schematically show the optimal compression range for constant, non-constant and air-assisted cushion stiffness. In these figures compression is shown by x-axis 60, whereas pressure is indicated by y-axis 62. Line 64 generally shows minimal pressure for sealing, line 66 generally shows the maximum (tolerable) pressure at which red marks may form on a user's face. The optimal compression range 68 is within boundaries 60a and 60b.

As indicated in FIG. 7a, the compression of the cushion should be in a rather small optimal compression range 68 for constant cushion stiffness, i.e. compression 70. As may be derived from FIG. 7b, a non-constant cushion compression stiffness again indicated by line 70 significantly increases the optimal compression range 68 and assists in realizing a compression in all places in the optimal compression range. This tailored stiffness however only performs well for a certain/specific value CPAP pressure.

For an optimal performance, the cushion stiffness needs to be adapted for different CPAP pressures. This case is shown in FIG. 7c having a broad optimal compression range within lower and upper boundaries 60a and 60b. Hence, the advantages of the present patient-contacting element 10 as well as the patient interface 12 comprising such a patient-contacting element 10 are proper sealing and giving the mask a stable position with respect to the user's 50 face. Therefore a secondary structure, such as forehead support 24 (compare FIG. 2a), may be avoided as this secondary structure will lead to lower pressure peaks unless made very soft. If this secondary structure, however, is made too soft it will become unstable, unless stabilized by an internal pressure as proposed herein.

The part of the silicon cushion 10 which is not supported by a secondary structure, such as any kind of cushion support structure, will very easily lose the contact with the face due to wrinkling or other stiffness effects (e.g. when stretch is needed to follow the facial contour) because there is no driving force towards the face at all as soon as the CPAP pressure penetrates between the cushion 10 and the face of the user 50. In contrast to this, the present cushion material will add a small extra pressure in the face direction. Additional to this, the substantially air-tight outer layer of the cushion can be chosen very soft and put under a pre-stress (by compressing the cushion inside material) for avoiding wrinkles.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A patient-contacting element for a patient interface for delivering a flow of gas to a user, said patient-contacting element being configured to provide a substantially air-tight seal with the user's skin during use and comprises:
   an inlet for receiving at least part of the flow of gas,
   at least one gas-permeable element that is disposed within the patient-contacting element and arranged in fluidic communication with the inlet,
   a first layer of an air-tight material that is arranged between the at least one gas permeable element and an inner space of the patient-contacting element for receiving a nose and/or a mouth of the user, wherein the air-tight material has a plurality of openings therein for allowing the passage of the gas directly between the inner space and the at least one gas-permeable element, and a second layer of an air-tight material that is arranged between the at least one gas-permeable element and an outer space of the patient-contacting element which is not in fluidic communication with the flow of gas during use, wherein the at least one gas-permeable element is in direct contact with the first layer of the air-tight material on a side of the layer of the air-tight material that is opposite the inner space.

2. The patient-contacting element according to claim 1, comprising at least one further layer of an air-tight material covering at least a portion of the at least one gas-permeable element.

3. The patient-contacting element according to claim 1, wherein the inlet opens out directly into the at least one gas-permeable element in order to provide at least part of the flow of gas directly to the at least one gas-permeable element.

4. The patient-contacting element according to claim 1, wherein the patient-contacting element is a cushion.

5. The patient-contacting element according to claim 1, wherein the at least one gas-permeable element comprises a foam and/or a stack of spacer fabrics.

6. The patient-contacting element according to claim 5, wherein the foam is an open cell foam.

7. The patient-contacting element according to claim 1, wherein a shape of the at least one gas-permeable element is adapted to contour of a user's face or head.

8. The patient-contacting element according to claim 1, wherein properties of the at least one gas-permeable element vary along the at least one gas permeable element.

9. The patient-contacting element according to claim 1, wherein the patient-contacting element comprises a plurality of gas permeable elements.

10. The patient-contacting element according to claim 1, comprising a third layer which covers at least a portion of the patient-contacting element and provides the substantially air-tight seal with the user's skin during use, wherein the third layer is not directly connected to the at least one gas-permeable element.

11. The patient-contacting element according to claim 10, wherein the third layer comprises a polymer film, a polymer membrane, a closed cell foam and/or a coated textile fabric.

12. The patient-contacting element according to claim 11, wherein the polymer film is a polyurethane film or silicone film.

13. The patient-contacting element according to claim 1, further comprising one or more of a forehead pad, a headgear and a cheek-mounted support.

* * * * *